United States Patent [19]

Zimmerman

[11] Patent Number: 5,410,918

[45] Date of Patent: May 2, 1995

[54] AMBIENT AIR SAMPLER

[75] Inventor: Patrick R. Zimmerman, Boulder, Colo.

[73] Assignee: University Corporation for Atmospheric Research, Boulder, Colo.

[21] Appl. No.: 930,157

[22] Filed: Aug. 13, 1992

[51] Int. Cl.$^6$ .............................................. G01N 1/24
[52] U.S. Cl. ..................... 73/864; 73/170.28; 73/863.31; 73/864.34; 73/864.31
[58] Field of Search ................. 73/864, 864.34, 864.35, 73/863.31, 170.28, 864.31

[56] References Cited

U.S. PATENT DOCUMENTS

| | | | |
|---|---|---|---|
| 2,489,337 | 11/1949 | Sperling | 73/170.28 X |
| 2,906,125 | 9/1959 | Jewett, Jr. | 73/864.31 |
| 2,943,490 | 7/1960 | Melton | 73/864.31 |
| 3,063,296 | 11/1962 | Huch et al. | 73/864.31 |
| 3,077,729 | 2/1963 | Froehlich et al. | 73/170.28 X |
| 3,724,271 | 4/1973 | Morrissey et al. | 73/29.02 |
| 4,085,973 | 4/1978 | Payne | 73/864.31 X |
| 4,226,115 | 10/1980 | Williams et al. | 73/170.28 X |

FOREIGN PATENT DOCUMENTS

| | | | |
|---|---|---|---|
| 25000 | 10/1969 | Japan | 73/170.28 |
| 11797 | 3/1971 | Japan | 73/170.28 |
| 917080 | 1/1963 | United Kingdom | 73/864.34 |
| 2080229 | 2/1982 | United Kingdom | 73/170.28 |
| 887995 | 12/1981 | U.S.S.R. | 73/864.34 |

Primary Examiner—Tom Noland
Attorney, Agent, or Firm—Duft, Graziano & Forest

[57] ABSTRACT

An ambient air sampler is pivotally mounted to a tether of a balloon-borne sampling device. The air sampler includes an inlet for receiving atmospheric gas samples and a pump for moving samples to one of a number of sample bags. A remotely-controlled valve is used to selectively determine which of the sample bags receives the sample. A pivotal mounting of the air sampler with respect to the tether includes an axle which is stationarily positioned on the tether and bearings which rotatably connect to the axle mounted to a mounting plate onto which the air sampler is secured.

16 Claims, 4 Drawing Sheets

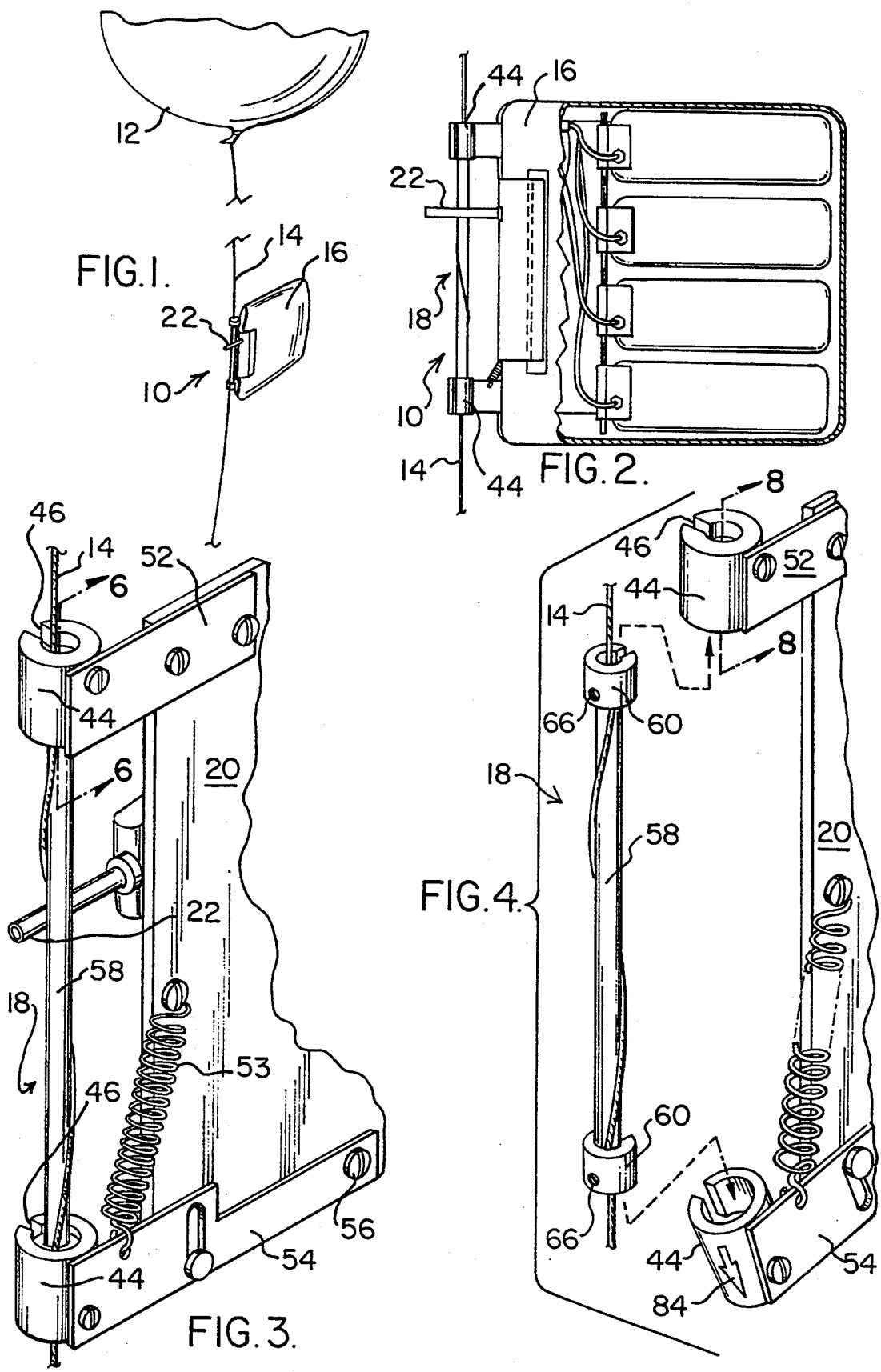

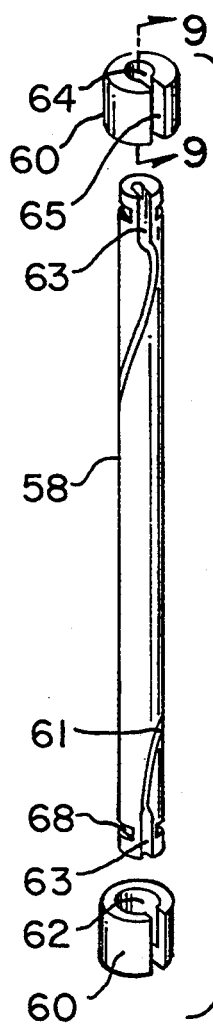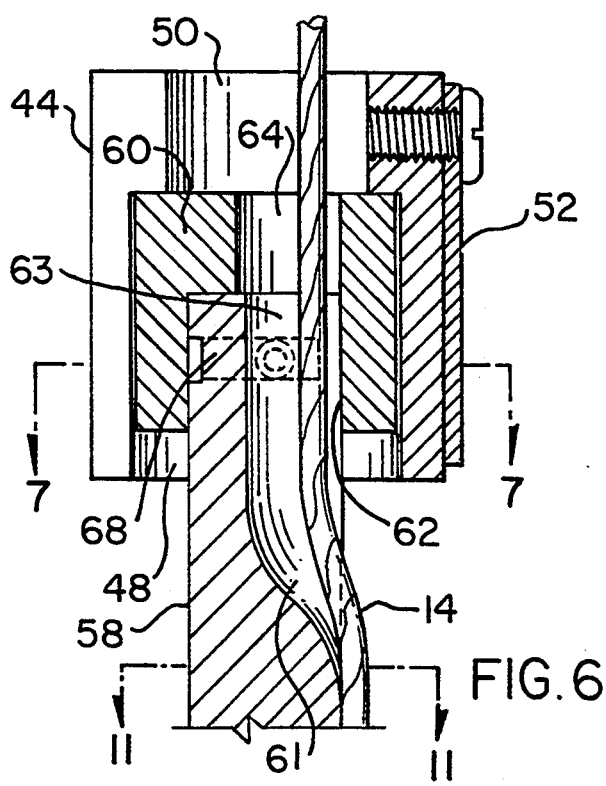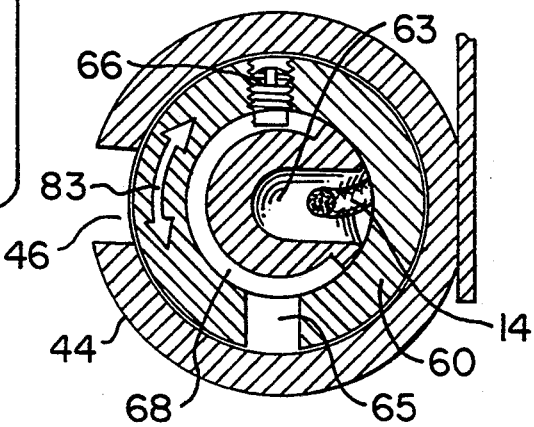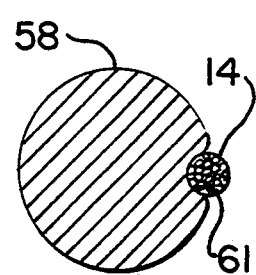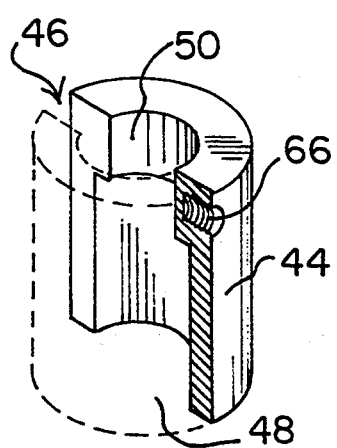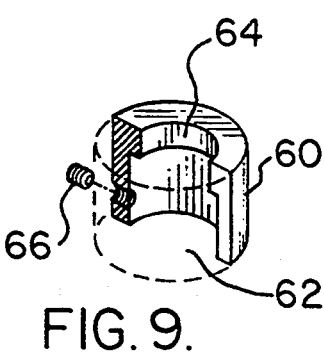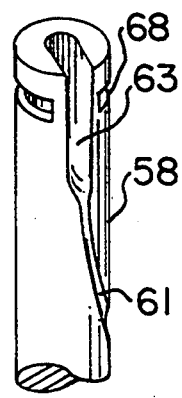

AMBIENT AIR SAMPLER

GOVERNMENT FUNDED INVENTION

This invention was made with Government support under Agreement No. ATM-8709659 awarded by the National Science Foundation. The Government has certain rights in this invention.

FIELD OF THE INVENTION

The present invention relates to methods and devices for sampling trace gas concentrations at various levels in the atmosphere. More particularly, the invention relates to balloon-borne gas sampling methods and devices for analyzing trace gases which may be present in the earth's atmosphere. The invention may also be used to determine trace gas fluxes for trace gases which have their sources or sinks at the surface of the earth vegetation canopies, and/or at tree or other organic growth areas, which are at relatively low altitudes.

PROBLEM

It has previously been difficult to measure trace gases from vegetation canopies or from other low altitudes near the ground. Such information has many scientific applications in atmospheric research. In getting the most complete information available, it is appropriate to have information both from high altitude measurements, based on aircraft sampling schemes, as well as low altitude or ground based measurements. Ground based samples alone are difficult to use to characterize representative free tropospheric concentrations because they can be unduly influenced by strong local sources. Aircraft sampling schemes are best to assess concentrations in the free troposphere. However, aircraft operation is often restricted and excluded near the ground or in proximity to a surface source which must be characterized. In addition aircraft typically travel so fast that it is difficult for them to generate vertical profiles that can be used to characterize fluxes from small scale (100 $m^2$–5 $km^2$) sources.

For trace gases which have local regional sources or relatively small area-wide sources (such as a landfill or hazardous waste disposal site), the vertical gradient of the trace gas of interest is often quite steep. That is, the change in concentration with altitude is the greatest close to the surface. At altitudes above a few hundred meters, the concentrations do not change very much. One way to estimate the flux is to carefully define the vertical gradient. Tethered balloons provide an excellent platform for these types of measurements. They can be suspended over an area for long enough to characterize the meteorological mixing elements (typically about one-half [½] hour).

Several schemes have been used in attempts to sample in the low altitudes. The most successful of these include towers and tethered balloons. Of these two options, tethered balloons provide more flexibility to easily vary deployment areas. They have the advantage of easily being able to reach 1,000 meters or more. One of the major limitations of tethered balloons is that their operational complexity and logistical support requirements increase rapidly as their size increases to allow larger instrument packages or payloads. Therefore, the ideal payload should be as light as possible.

Modern tether lines such as those made from Kevlar have an extremely high strength to weight ratio. Unfortunately, these lines are also susceptible to breakage from abrasion, twisting, and kinking stresses. Therefore, the instrument package attachment system for such tethered balloons is very important. It must be lightweight and simple to operate and yet not allow the instrument package to slip, causing abrasion of the tether line. The instrument package must also be free to rotate with the wind direction around the line to prevent the tether line from twisting. Finally, the instrument package and package attachment system together should not have undue wind resistance which might lead to tether line kink stresses and increasing chance of the tether line becoming entangled in trees as the package attachment system is blown downwind.

Many of the trace gases of interest are present in the atmosphere at extremely low concentrations. In addition, many are very reactive and difficult to collect without compromising the sample. For this reason, an air sampler of the instrument package must be suspended some distance below the balloon. Also, the materials of construction of an instrument package for a balloon are critical. For example, the instrument package hereinafter described was developed specifically to collect air samples for trace hydrocarbon determination. For this reason, no rubber can be used near the air sampler and in addition, the only allowable materials in the flow path of the sample system are stainless steel, teflon that is scrupulously clean and tested for out-gassing, and a limited amount of anodized aluminum. Many of the materials of construction could be easily varied to accomplish specific trace gas requirements. For hydrocarbons, it is also important that gas samples collected in teflon sample bags be shielded from light and that they be transferred to stainless steel canisters for long-term storage.

At times it is desirable to simultaneously collect samples along a vertical profile. In this case the sample packages must be extremely lightweight and simple to attach to the tether line so that several may be deployed along the length of the tether line.

SOLUTION

The above problems are solved, and a technical advance achieved in the field by the ambient air sampler of the present invention. The ambient air sampler is mounted to a tether line of a balloon to establish a lightweight instrument package for collection of air samples. The air sampler, used in conjunction with and attached to the tethered balloon, collects air samples within or above vegetation canopies comprised of trees, grass, brush or vegetation, or other surface source emitting gas into the atmosphere. The samplers can also be used to establish the vertical homogeneity of trace gas composition. A package attachment system pivotally mounts the air sampler to allow it to pivot about the tether line without causing the tether line to twist. An aerodynamic cover shrouds the entire air sampler to minimize drag. Several of the air samplers can be deployed simultaneously along the line in order to collect integrated vertical profiles.

The air sampler includes a pump for moving gas received at a sampler inlet past a switching valve and into one of several sampling bags. A wireless microphone indicates to the operator that the pump is operating and when valve switching functions occur.

The attachment system includes a stationary axle which is secured to the tether line at respective ends of the axle. End caps fit over the ends of the axle and are received by bearings secured to a mounting plate of the air sampler. The bearings allow the air sampler to rotate about the end caps of the axle while the tether line is held stationary with the axle. Alternatively the package bearing surface could be located anywhere along the length of the axle as long as it is slotted to accept the tether line.

Other aspects, features and details of the present invention can be more completely understood by reference to the following detailed description of a preferred embodiment, taken in conjunction with the drawings, and from the appended claims.

DESCRIPTION OF THE DRAWING

FIG. 1 is a fragmentary perspective view of an ambient air sampler of the invention attached to a tether line of a balloon;

FIG. 2 is a fragmentary elevational view of the invention shown in FIG. 1 attached to the tether line;

FIG. 3 is a fragmentary perspective view of the attachment system of the invention connecting the air sampler to the tether line;

FIG. 4 is a fragmentary exploded perspective view of the attachment system similar to FIG. 3 showing the release of the air sampler from the tether line;

FIG. 5 is an enlarged exploded perspective view of an axle of the attachment system;

FIG. 6 is an enlarged sectional view taken along line 6—6 of FIG. 3;

FIG. 7 is an enlarged sectional view taken along line 7—7 of FIG. 6;

FIG. 8 is an enlarged sectional view of an end cap of the attachment system;

FIG. 9 is an enlarged sectional view taken along line 9—9 of FIG. 5;

FIG. 10 is an enlarged perspective view of one end of the axle of the attachment system;

FIG. 11 is a sectional view taken along line 11—11 of FIG. 6;

DESCRIPTION OF THE PREFERRED EMBODIMENT

Figure 17:
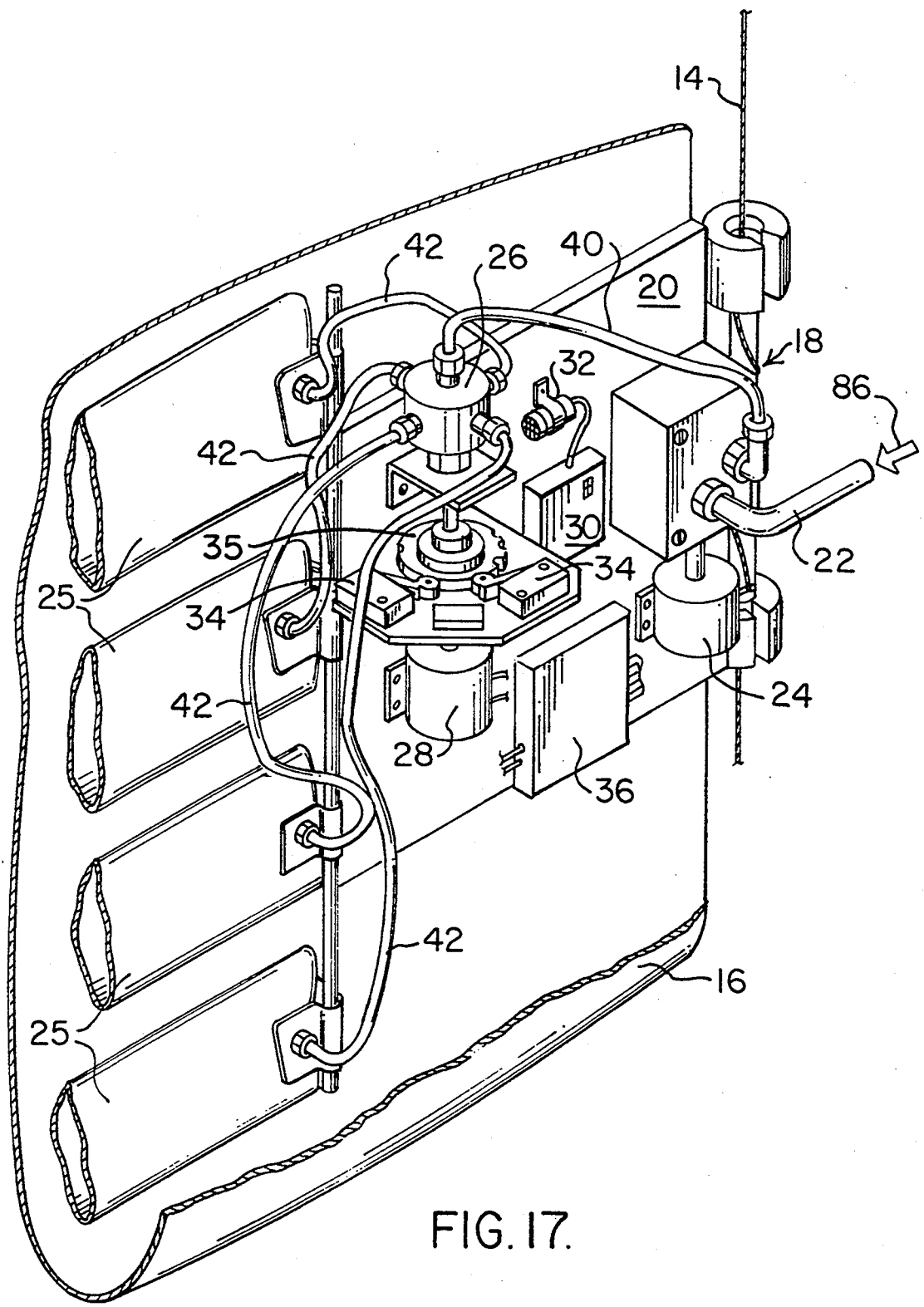
FIG. 17 is a fragmentary perspective view of the air sampler.

An ambient air sampler 10 for collecting trace gases from the atmosphere is pivotally mounted by an attachment system 18 to a tether line 14 of a weather balloon 12 as shown in FIGS. 1, 2 and 17. The air sampler 10 could be mounted to a line on a tower as well. The air sampler 10 is covered by an envelope 16 which minimizes the air drag of the air sampler 10. The air sampler 10 is thereby free to move about the tether line 14 as wind direction changes.

As shown in FIG. 17, mounting plate 20 has the principal components of the air sampler 10 connected thereto. An inlet 22 is in air flow communication with a pump 24. The pump 24 draws an atmospheric sample into the inlet 22 and directs the sample along feed tube 40 to a selector valve 26. From the selector valve 26, the sample is directed by distribution tubes 42 into one of a plurality of sampling bags 25, depending on the position of the selector valve 26.

The operator of the air sampler 10 is in radio communication with the air sampler through a transceiver 30. A wireless microphone 32 is used to supply audio indications to the operator concerning the operation of the pump 24 and to confirm any change in position of the selector valve 26. A servo motor 28 is remotely activated, via transceiver 30, to change the position of the selector valve 26. A battery (not shown) supplies electrical power to the air sampler 10. The battery includes 12 AA size nickel cadmium rechargeable batteries.

A controller 36 receives instruction signals from the transceiver 30 and operates the selector valve 26 and the pump 24. Microswitches 34 provide the controller 36 with an indication of the position of the selector valve 26. The position of selector valve 26 is sensed by microswitches 34 via detents in wheel 35, which is attached to the servo motor shaft.

A preferred embodiment of the attachment system 18 is shown in FIGS. 3–11. The mounting plate 20 includes an upper mounting arm 52 fixedly connected to an upper cylindrical bearing 44 and a lower spring-loaded mounting arm 54 connected about a pivot 56 to a lower cylindrical bearing 44, as shown in FIGS. 3 and 4. Spring 53 biases the lower spring-mounted arm 54 into a locked position, holding an axle 58 between the bearings 44, as shown in FIGS. 3 and 8.

As shown in FIGS. 5 through 11, tether line 14 is wound about the axle 58 and secured relative thereto by a pair of end caps 60. An end of the axle 58 is inserted into the cap 60. The axle 58 also includes a helical line groove 61 formed on the outer surface of the axle 58, which line groove 61 guides and seats the tether line 14 relative to the axle 58. A line slot or notch 63 at each end of the axle 58 receives the tether line 14 from the line groove 61. The tether line 14 is positioned relative to the axle 58 by the end cap 60. The tethering line 14 is positioned as it enters and exits the line slot 63 generally parallel to a longitudinal axis of the axle 58. The end cap 60 is secured over the end of the axle 58 by a set screw 66. The set screw 66 enters a groove 68 formed circumferentially about either end of the axle 58 to frictionally secure the end cap 60 relative to the axle 58.

As shown in FIGS. 5 through 9, each of the end caps 60 are cylindrically formed and include an axle inlet 62 which fits over the ends of the axle 58. A counter bore in the end cap 60 defines a line outlet 64 from which the tether line 14 extends into and then away from the attachment system 18. The tether line 14 passes through a line inlet 65 into each of the end caps 60.

As shown in FIGS. 7 and 8, each of the bearings 44 includes a line inlet slot 46 to receive the tether line 14 counter bore bearing surface 48. The counter bore bearing surface 48 receives the end caps 60 in a rotatable mating relationship. The bearing housings 44 also include a tether line outlet 50 permitting the tether line 14 to extend upwardly and downwardly away from the attachment system 18. The upper bearing 44 is fixedly connected to the mounting plate 20 and secures one end cap 60 of the axle 58. The lower bearing 44 moves away from its end cap 60 to connect or release the axle 58 and end cap 60 from the attachment system 18, as shown in FIGS. 3 and 4. Each of the bearings 44 slidably and rotatably receive one of the end caps 60 to allow for pivotal movement of the entire air sampler 10 about the axle 58 and caps 60.

Figure 12:
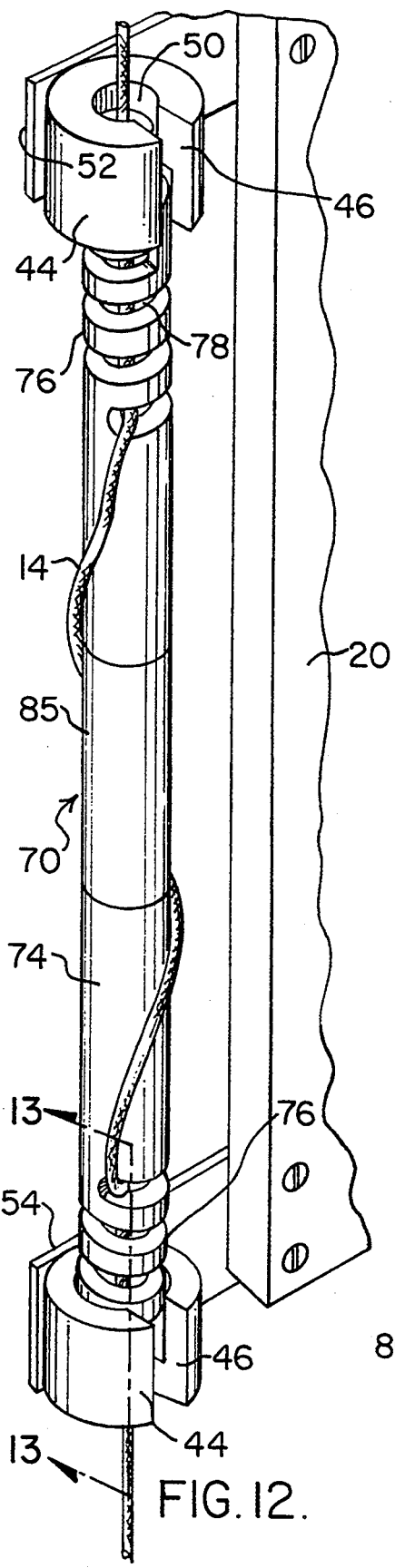
FIG. 12 is a fragmentary perspective view of an alternative attachment system.
Figure 13:
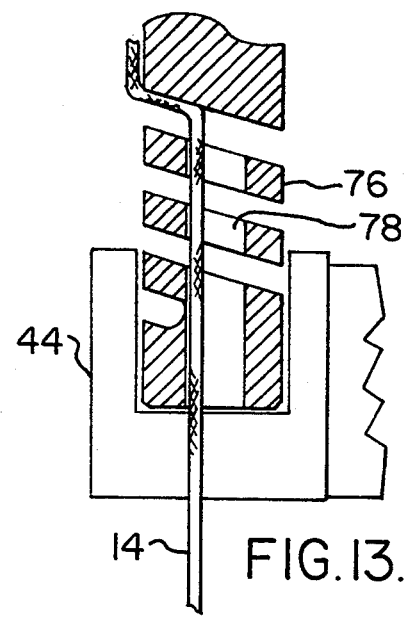
FIG. 13 is an enlarged fragmentary sectional view taken along line 13—13 of FIG. 12.

An alternative embodiment of an attachment system 70 is shown in FIGS. 12–16. In this alternative embodiment, no lower spring-loaded arm 54 is required. An axle 74 includes a spring-like spiral 76 which can be compressed. A bore 78 along the spiral allows for the tether line 14 to pass out of the spiral 76. As shown in FIG. 13, the bearings 44 receive the spiral 76 without the need of an end cap 60. This arrangement can also be used in conjunction with a lower spring-loaded mounting arm as shown in the preferred embodiment.

Figure 14:
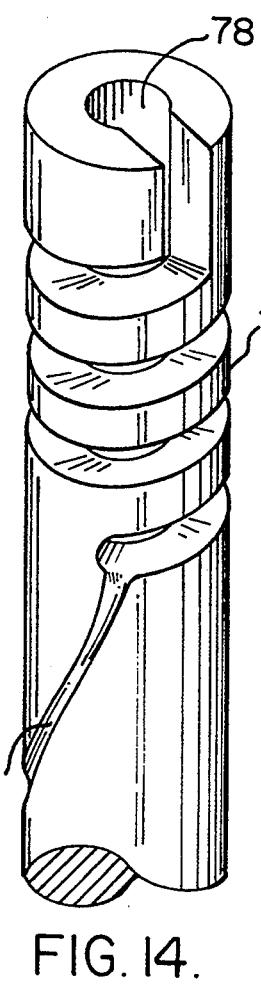
FIG. 14 is an enlarged fragmentary perspective view of an axle of the attachment system shown in FIG. 12.

As shown in FIG. 14, a line groove 80 is formed spirally about an outer surface of the axle 74 to help align and position the tether line 14 relative to the axle 78.

Figures 15, 16:
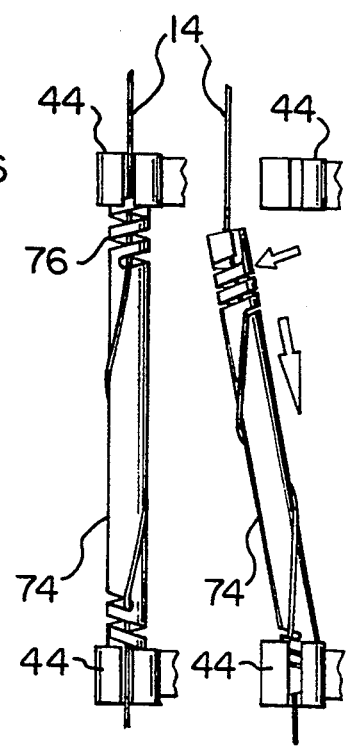
FIGS. 15 and 16 show the axle of the attachment system shown in FIG. 12 and a connection to bearings of the air sampler.

As shown in FIGS. 15 and 16, the axle 74 is compressed and deflected relative to the bearings 44 to connect or release the attachment system 70. Axle 74 also typically includes a segment 85 coated with a non-slip material such as heat-shrink tubing. In addition air sampler 10 can be operated in a single sample mode without a switching valve and triggered by a timer circuit instead of transceiver 30.

Although the present invention has been described with particularity, it is understood that the present disclosure has been made by way of example, and changes in detail or structure may be made without departing from the spirit of the invention, as defined in the appended claims.

I claim:

1. An ambient air sampler including a balloon attached to a tether line, comprising:
   attachment means including first connection means fixedly connected to said tether line and second connection means rotatably connected to said first connection means;
   wherein said first connection means includes an axle about which said tether line is wound, said axle having a first end and a second end, each of said ends of said axle having means associated therewith for securing said tether line relative to said axle.

2. The invention as defined in claim 1 wherein said attachment means includes:
   an end cap which receives said tether line and which mounts over each of said ends of said axle; and
   a bearing which receives said tether line and matingly fits over said end cap and pivots about said end cap, said bearing being operatively connected to said air sampler.

3. The invention as defined in claim 2 wherein said axle includes a circumferential groove near each end thereof for receiving a set screw which passes through said end cap to position said end cap fixedly relative to said axle.

4. The invention as defined in claim 2 wherein one of said bearings is selectively movable between a position to pivotally receive one of said end caps in a connected position and a second position away from said end cap to release said axle and said end cap from the air sampler.

5. The invention as defined in claim 1 wherein said attachment means further includes a helical spring integrally formed at each end of said axle which receives said tether line along a central bore thereof, said tether line and helical spring being received by a pair of bearings operatively connected to said air sampler, said helical spring being pivotally received and connected to each of said bearings.

6. An ambient air sampler including a balloon attached to a tether line, comprising:
   a central axle fixedly connected at ends thereof to said tether line; and
   means for pivotally connecting said air sampler to said axle;
   wherein said means for pivotally connecting said air sampler to said axle include:
   end caps which have means for receiving said tether line and securing said tether line relative thereto, said end caps selectively receiving said tether line; and
   cylindrical bearings mounted on said air sampler which receive said tether line anal which fit over said end caps in a male/female pivotal connection to thereby allow pivotal movement of said air sampler relative to said axle and tether line.

7. The invention as defined in claim 6 wherein said air sampler is covered by an aerodynamic envelope to minimize air drag of said air sampler.

8. The invention as defined in claim 6 wherein said air sampler includes:
   an inlet for receiving an atmospheric gas sample;
   pump means for drawing said gas sample into said inlet; and
   distribution means for receiving said sample from said pump means and distributing said sample into any one of a plurality of sample bags.

9. The invention as defined in claim 8, further including a transceiver operatively connected to said pump means and said distribution means for remotely controlling the operation thereof.

10. The invention as defined in claim 8, further including a timer operatively connected to said pump means for controlling the operation thereof.

11. The invention as defined in claim 6, further including a microphone, operatively connected to a radio transmitter, for transmitting audio indications of the status of said air sampler to remote receiving means.

12. An ambient air sampler including a balloon attached to a tether line, comprising:
   an axle secured to said tether line by end caps selectively secured thereto, said end caps selectively receiving said tether line; and
   cylindrical bearings mounted on said air sampler which receive said tether line and fit over said end caps in a male/female pivotal connection to thereby allow pivotal movement of said air sampler relative to said axle and said tether line.

13. The invention as defined in claim 12 wherein said air sampler is covered by an aerodynamic envelope to minimize air drag of said air sampler.

14. The invention as defined in claim 12 wherein said air sampler includes:
   an inlet for receiving an atmospheric gas sample;
   pump means for drawing said gas sample into said inlet; and
   distribution means for receiving said sample from said pump means and distributing said sample into any one of a plurality of sample bags.

15. The invention as defined in claim 14, further including a transceiver operatively connected to said pump means and said distribution means for remotely controlling the operation thereof.

16. The invention as defined in claim 12 wherein a microphone, operatively connected to a radio transmitter, is used to transmit audio indications of the status of said air sampler to remote receiving means.

* * * * *